US008676597B2

(12) United States Patent
Buehler et al.

(10) Patent No.: US 8,676,597 B2
(45) Date of Patent: Mar. 18, 2014

(54) METHODS AND SYSTEMS FOR MAPPING HEALTHCARE SERVICES ANALYTICS FOR VOLUME AND TRENDS

(75) Inventors: Hans Buehler, Burlington, VT (US); Hans-Joerg Fischer, Burlington, VT (US); Timothy Fitzgerald, Burlington, VT (US); David Merkx, Burlington, VT (US); Eric Larson, Burlington, VT (US); Brent Ogle, Burlington, VT (US)

(73) Assignee: General Electric Company, Schenectady, NY (US)

( * ) Notice: Subject to any disclaimer, the term of this patent is extended or adjusted under 35 U.S.C. 154(b) by 327 days.

(21) Appl. No.: 12/647,811

(22) Filed: Dec. 28, 2009

(65) Prior Publication Data

US 2011/0161096 A1 Jun. 30, 2011

(51) Int. Cl.
*G06Q 50/00* (2012.01)
(52) U.S. Cl.
USPC .................................................. 705/2; 705/3
(58) Field of Classification Search
USPC ....................................................... 705/2–3
See application file for complete search history.

(56) References Cited

U.S. PATENT DOCUMENTS

| 5,652,842 | A | 7/1997 | Siegrist, Jr. et al. | |
|---|---|---|---|---|
| 6,014,629 | A * | 1/2000 | DeBruin-Ashton | 705/2 |
| 2002/0026329 | A1* | 2/2002 | Saito et al. | 705/3 |
| 2006/0020424 | A1* | 1/2006 | Quindel | 702/183 |
| 2007/0106537 | A1 | 5/2007 | Moore | |
| 2007/0106751 | A1 | 5/2007 | Moore | |
| 2007/0116037 | A1 | 5/2007 | Moore | |
| 2007/0168461 | A1 | 7/2007 | Moore | |
| 2009/0099865 | A1 | 4/2009 | Zak et al. | |

OTHER PUBLICATIONS

Australian Indigenous HealthInfoNet, "Map of Aboriginal Medical Services in Australia," http://www.healthinfonet.ecu.edu.au/health-systems/health-workers/organisations/map-of-aboriginal-medical-services-in-australia, retrieved on Jun. 14, 2010 (1 page).
City Search, search results for "Austin, TX Metro Medical Services," http://triangle.citysearch.com/listings/austin-tx-metro/medical_services/81223_1916, retrieved on Jun. 14, 2010 (3 pages).
ESRI, "Analysis of Emergency Medical Service Calls for St. Johns County, Florida," http://www.esri.com/mapmuseum/mapbook_gallery/volume20/safety3.html, retrieved on Jun. 14, 2010 (1 page).
ESRI, "Emergency Medical Services," http://www.esricanada.com/english/1912.asp, retrieved on Jun. 14, 2010 (1 page).

* cited by examiner

*Primary Examiner* — Sind Phongsvirajati
(74) *Attorney, Agent, or Firm* — Hanley, Flight and Zimmerman, LLC

(57) ABSTRACT

Certain examples provide systems and methods for analysis and graphical visualization of healthcare services data. Certain examples provide a healthcare services analysis and visualization system. The system includes a data store to store data related to healthcare services provided in at least one geographic region. The system also includes a processor to retrieve and sort data from the data store based on one or more criteria, analyze the sorted data, and transform the sorted data into a geographical map representation of the healthcare services data. The system includes a user interface to display the geographical map representation of the healthcare services data and facilitate user review and interaction with the geographical map representation and the underlying healthcare services data.

18 Claims, 8 Drawing Sheets

METHODS AND SYSTEMS FOR MAPPING HEALTHCARE SERVICES ANALYTICS FOR VOLUME AND TRENDS

BACKGROUND

Providers of medical services, whether as a hospital department or a stand alone group, find themselves in an increasingly competitive environment. Each provider is trying to capture profitable services to care for their patient populations. Medical service provider departments are often unaware of particular needs, habits, and circumstances of patients in their local markets.

BRIEF SUMMARY

Certain examples provide systems and methods for analysis and graphical visualization of healthcare services data.

Certain examples provide a healthcare services analysis and visualization system. The system includes a data store to store data related to healthcare services provided in at least one geographic region. The system also includes a processor to retrieve and sort data from the data store based on one or more criteria, analyze the sorted data, and transform the sorted data into a geographical map representation of the healthcare services data. The system includes a user interface to display the geographical map representation of the healthcare services data and facilitate user review and interaction with the geographical map representation and the underlying healthcare services data.

Certain examples provide a method for analysis, mapping, and visualization of healthcare services data. The method includes retrieving healthcare services data from a data store; sorting the retrieved healthcare services data, using a processor, based one or more criteria; analyzing the sorted data, using a processor, according to one or more criteria; transforming the sorted data into a geographical map representation of the healthcare services data using a processor; displaying the geographical map representation of the healthcare services data via a user interface; and facilitating user review and interaction with the geographical map representation and the underlying healthcare services data via the user interface.

Certain examples provide a computer-readable storage medium having a set of instructions stored thereon which, when executed, instruct a processor to implement a healthcare services analysis and visualization system. The system includes a data store to store data related to healthcare services provided in at least one geographic region. The system also includes a processor to retrieve and sort data from the data store based on one or more criteria, analyze the sorted data, and transform the sorted data into a geographical map representation of the healthcare services data. The system includes a user interface to display the geographical map representation of the healthcare services data and facilitate user review and interaction with the geographical map representation and the underlying healthcare services data.

Figure 1:
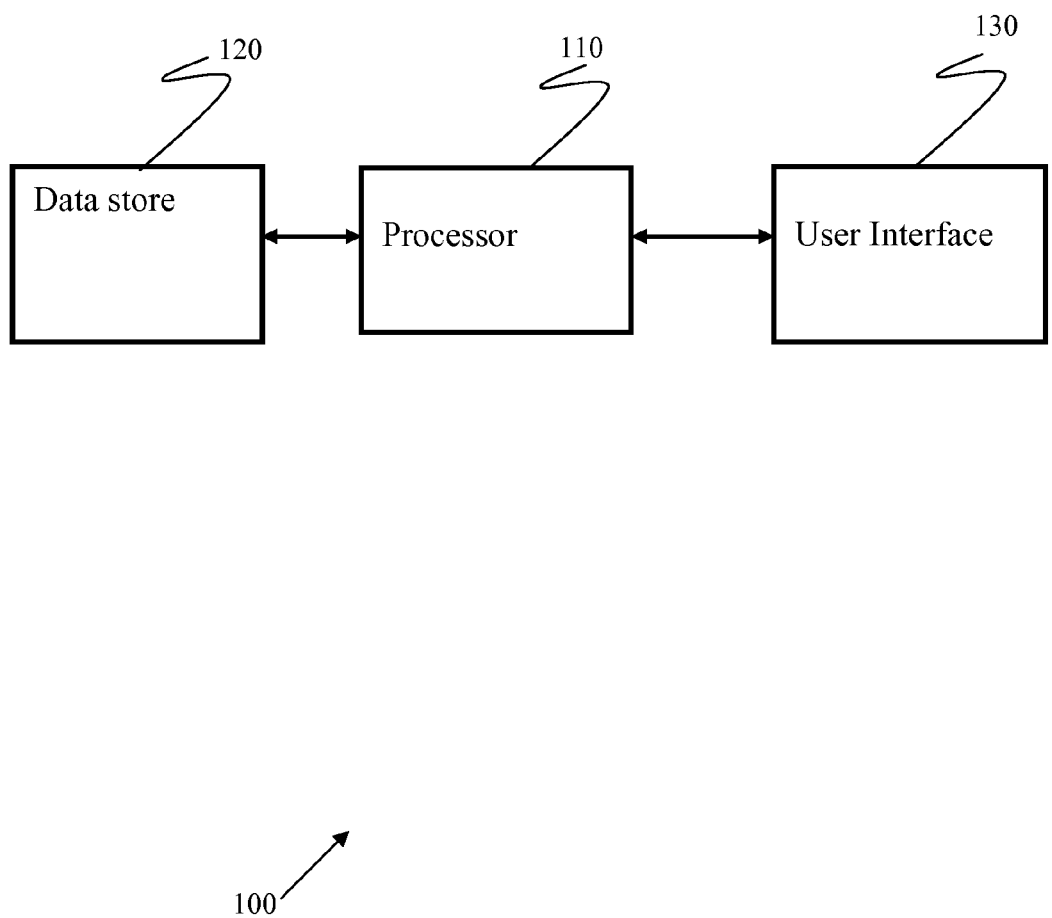
FIG. 1 illustrates an example healthcare analytics system to provide mapping and analysis of healthcare data, such as healthcare services data.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

Certain examples provide a map-based analytical tool to visualize and analyze healthcare services. Certain examples provide systems and methods to map healthcare services to generate volume, trends, and/or other analytics. Certain examples provide a healthcare analytics in a geographical map representation including measurements of clinical information such as procedure outcome, diagnosis, quality of service, order appropriateness, etc. Certain examples provide a geographic map based visual analytic tool allowing healthcare service providers to perform various marketing analytics, marketing program targeting, and effectiveness measuring, such as procedure outcome, diagnosis, quality of service, and/or order appropriateness.

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements in an at least one example is hereby expressly defined to include a tangible medium such as a memory, DVD, CD, etc. storing the software and/or firmware.

Providers of medical services, such as a hospital department, a stand alone medical care group, etc., would benefit from an ability to analyze trends regarding business origination, such as from primary care referring physician offices, and where a patient goes for his/her initial medical exam, for example. Medical services providers also would benefit from an ability to analyze trends regarding patient residence in relation to facility location to help determine how effective providers are and/or can be in servicing a local market, for example. Certain examples provide tools to assist providers measuring effectiveness and/or quality of medical service offerings.

Certain examples draw a type of data specified by the user (e.g., Top Five (5) Study Types Performed, Top Ten (10) Diagnoses, Patient Income Level, Number of Studies Performed, etc.) from existing data in a system, such as a Radiology Information System (RIS). The complete range of data is limited only by what is collected by the RIS system as part of its everyday activity and what can be logically associated with a geographical location, for example. The data is queried from the RIS database along with a date and time that the data was recorded and/or an indicated event occurred, as well as a related address of a type that is user-selected. This address type can be Provider Address or Patient Address, for example.

The data is then sorted by the included date/time. Sorting allows the user to specify specific one or more time range(s) to review and/or to review all of the data in a time-lapse format, for example. Both of these features provide support for trend analysis of the data.

The data and associated addresses are then fed or otherwise provided to one of several electronic map services, such as Microsoft MapPoint™ or Google™ Maps. The mapping service arranges the data geographically. The mapping service is used to render the data on a geographical map according to its associated region. The display can be configured in several formats, including pie charts centered over an applicable region or region coloring, for example. One or more regions can be statically set (always display cities as regions, for example) and/or can be variable by zoom level on the map (e.g., show cities as regions when zoomed to state level, but render states as regions when zoomed to country level, etc.).

For example, a user can request to show Average Patient Income Level for all patients who had studies performed in the last year. The user can request to regionalize the data by patient address and show the data by coloring a region with more intense colors as income levels increase. The user can then move through the data year by year to observe changing trends in income levels, possibly to help determine where a new radiology center could be built.

As another example, a user can request to show Top 5 Most Performed Study Types over the lifetime of the RIS. The data can be regionalized based on a requesting healthcare provider address and can be displayed as one or more pie charts, for example.

Certain examples allow the marketing department of a healthcare services provider to see and analyze a geographic origin of their business profile and measure changes in business volume and geographic origin over time through visual mapping elements. A healthcare services provider can analyze geographic proximity to referring physicians and patient residences to understand and trend from where their business is originating. A healthcare services provider can provide a visual representation of a volume of performed procedures based on patient residence and determine trending over time. A user can view trending data month by month and click forward to see how a profile of pin points on the map changes when a new health care services center opens, for example.

For example, large city hospitals that provide radiology services often wonder what the effect of newly opening competitive imaging centers has on a community. Often, these large hospitals do not have a good sense for whether they are losing business.

Using geographic analysis, "under served" geographic regions can be identified which produce low volume of business so that marketing of healthcare services can be targeted to certain regions. A mapping tool can quickly locate primary care offices in geographic areas of interest and their phone numbers and/or email addresses to proactively market healthcare services. In some examples, the mapping tool integrates with Internet Protocol (IP) and/or Internet-enabled phones to enable a user to call referring office(s) immediately. A mapping tool can provide a way to flag the marketing efforts to for an office, as well as an ability to track phone calls and emails initiated from within a system automatically. The tool can provide an ability to manually indicate other marketing efforts, for example.

In certain examples, effectiveness of individual marketing efforts to grow business from a particular geographic region can be measured. An impact of geographic referral trends upon opening of a new local competitive healthcare services centers and/or for new facilities opened by a requesting healthcare service provider can be analyzed. The tool can help a healthcare service provider understand if they have tapped into a new geographic area in the community and/or cannibalize existing services from existing facilities, for example.

Geographic map-based analytics can be used to provide a visual representation regarding from where healthcare services groups are getting their business and how this trends over time, specifically, for instance, when a new healthcare services center opens in the community (either their own center, or a competitive one, for example). Healthcare services business interaction can be analyzed by geographically available socio-economic data, for example.

In some examples, visual mapping tools can show a national and/or global volume of healthcare services procedures of various types (e.g., imaging, cardiology, etc.) and how volume relates to pay for performance (P4P) reimbursement and quality. Visual trending of this data helps provide an understanding of growth of procedures (e.g., drivers of healthcare costs) across the country to identify areas with high growth to be focused on to control growth of healthcare spending and P4P, for example.

Rather than simply reviewing text reports, geographic trending is provided in conjunction with radiology business data to create a visual business and planning aid.

In some examples, geographic analysis can be used in conjunction with radiology services marketing. Hospital radiology departments and stand alone imaging centers are in a competitive environment each trying to capture the profitable radiology services to patient populations. Radiology marketing departments can analyze trends regarding from which referring physician offices their business is originating when the patient goes for his or her initial medical exam. Radiology marketing departments can also analyze trends regarding where their patients reside and the location of their facilities to understand how effectively they are servicing the local market.

Certain examples provide a map-based visual analytic tool for radiology marketing departments to perform various marketing analytics, marketing program targeting, effectiveness measuring, etc. Marketing is allowed to see and analyze geographic origin of their business and measure changes in business volume and geographic origin over time through visual mapping elements, for example. Geographic proximity to referring physicians and patient residences is analyzed to understand and trend where business is originating. A visual representation of volume of imaging procedures is provided based on the patient residence, for example, and trending of the volume over time is enabled. For example, a user can view month by month and click forward and see how a profile of pin points on a geographic map changes when a new imaging center opens. Large city hospitals that provide radiology services, for example, can evaluate an effect of newly opening competitive imaging centers in the community and determine whether an opening results in a loss of business.

In certain examples, "under served" geographic regions that produce a low volume of radiology business can be identified to target marketing of radiology services to certain regions. The mapping tool quickly finds primary care offices in geographic areas of interest and their phone numbers/ emails to proactively market their radiology services, for example. The mapping tool can further integrate with IP phones to allow a user to call a referring office. The mapping tool provides a way to flag marketing efforts to the physician office, along with an ability to automatically track phone calls and emails initiated from within the system. Other marketing efforts can be manually indicated, for example.

Using the mapping tool, effectiveness of individual marketing efforts to grow business from a particular geographic region can be measured, for example. Additionally, an impact of geographic referral trends upon opening of a new local competitive imaging center or a new facility opened by the requesting organization can be analyzed. A user can understand if it has tapped into a new geographic area in the community or is instead cannibalizing existing radiology services from existing facilities. Map-based analytics can provide a visual representation of locations where radiology groups are getting their business and how the location(s) trend over time. Specifically, for instance, a user can visually review location and trends when a new imaging center opens in the community (either a user's own imaging center or a competitive one, for example). A user can analyze interaction of its own radiology business based on geographically available socio-economic data, for example.

Certain examples provide mapping tools to depict and analyze a growth of imaging procedures and healthcare spending. For example, visual mapping tools can show national and global volumes of imaging procedures of various types (e.g., CT, MRI, etc). Visual trending of imaging procedure data provides an understanding of growth of imaging procedures (e.g., drivers of healthcare costs) across the country to identify areas with high growth to be focused on to control growth of healthcare spending, for example.

In some examples, visual mapping tools can be used to help with population disease tracking. A geographic mapping analysis tool correlates imaging procedures and concentration of diseases by geographic location, for example. Disease trends can be determined from the gathered data.

FIG. 1 illustrates an example healthcare analytics system 100 to provide mapping and analysis of healthcare data, such as healthcare services data. The system 100 includes a processor 110, a data store 120, and a user interface 130. Healthcare services data is gathered and saved at the data store 120.

The data can be gathered manually and/or automatically by one or more healthcare practitioners, healthcare information systems, imaging systems, etc., and stored at the data store 120. Data gathered can be dictated and/or affected by user preference, for example. Data can include number and/or type of studies performed, diagnoses, patient income level, etc., gathered from a RIS, PACS, and/or other clinical information and/or billing system, for example. For example, using the processor 110, the data is queried from the RIS database along with a date and time that the data was recorded and/or an indicated event occurred, as well as a related address of a type that is user-selected. This address type can be a provider address or patient address, for example. Data can be sorted by location, date, time, and/or other criteria, for example, using the processor 110. The processor 110 provides the processed data to the user interface 130 (e.g., in the form of one or more indicators on a geographic map). The display via the user interface 130 can be configured in several formats, including pie charts centered over an applicable region or region coloring, for example. One or more regions can be statically set (always display cities as regions, for example) and/or can be variable by zoom level on the map (e.g., show cities as regions when zoomed to state level, but render states as regions when zoomed to country level, etc.).

In some examples, visual mapping tools can show a national and/or global volume of healthcare services procedures of various types (e.g., imaging, cardiology, etc.) and how volume relates to pay for performance (P4P) reimbursement and quality. Visual trending of this data helps provide an understanding of growth of procedures (e.g., drivers of healthcare costs) across the country to identify areas with high growth to be focused on to control growth of healthcare spending and P4P, for example. Rather than simply reviewing text reports, geographic trending is provided in conjunction with radiology business data to create a visual business and planning aid. Geographic map-based analytics can be used to provide a visual representation regarding from where healthcare services groups are getting their business and how this trends over time, for example.

Figure 2:
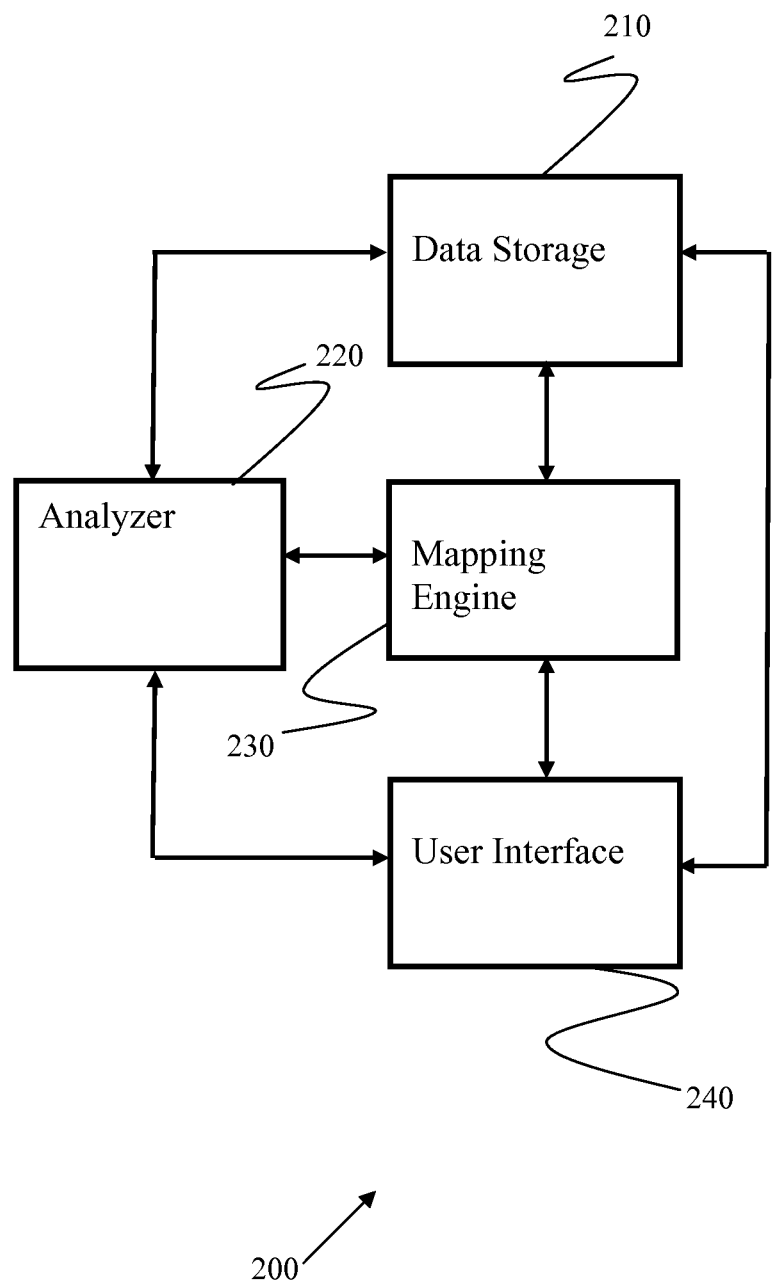
FIG. 2 illustrates an example healthcare services analytics system to provide geographical mapping and analysis of healthcare services data for one or more regions.

FIG. 2 illustrates an example healthcare services analytics system 200 to provide geographical mapping and analysis of healthcare services data for one or more regions. The system 200 includes a data store 210, an analyzer 220, a mapping engine 230, and a user interface 240. Clinical and/or healthcare service/performance data is stored in the data store 210. Data in the data store 210 is retrieved by the analyzer 220 to evaluate and determine trends, correlations, relationships, and/or other metrics based on the available data. Data and associated analysis can be organized based on provider, facility, region, and/or other criteria, for example. Analyzed data can be provided to the mapping engine 230 from the analyzer 220 and/or data store 210. The mapping engine 230 combines the data with geographical and/or other demographic information and provides the data in a graphical representation (e.g., a geographical map) to a user via the user interface 240. Via the user interface 240, the user can view raw data from the data store 210 and/or analyzer 220, geographically mapped data from the mapping engine 230, etc., and can drill down into one or more representations of data show on the user interface 240 map (e.g., pie charts, indicators (e.g., tacks), graphs, thumbnails, etc.). In some examples, a user can modify data and/or add additional data and/or comment via the user interface 240. Data generated by the mapping engine 230, analyzer 220, and/or via the user interface 240 can be stored at the data store 210 and/or routed to the analyzer 220 and/or an external system for further processing and/or external storage, for example.

Figure 3:
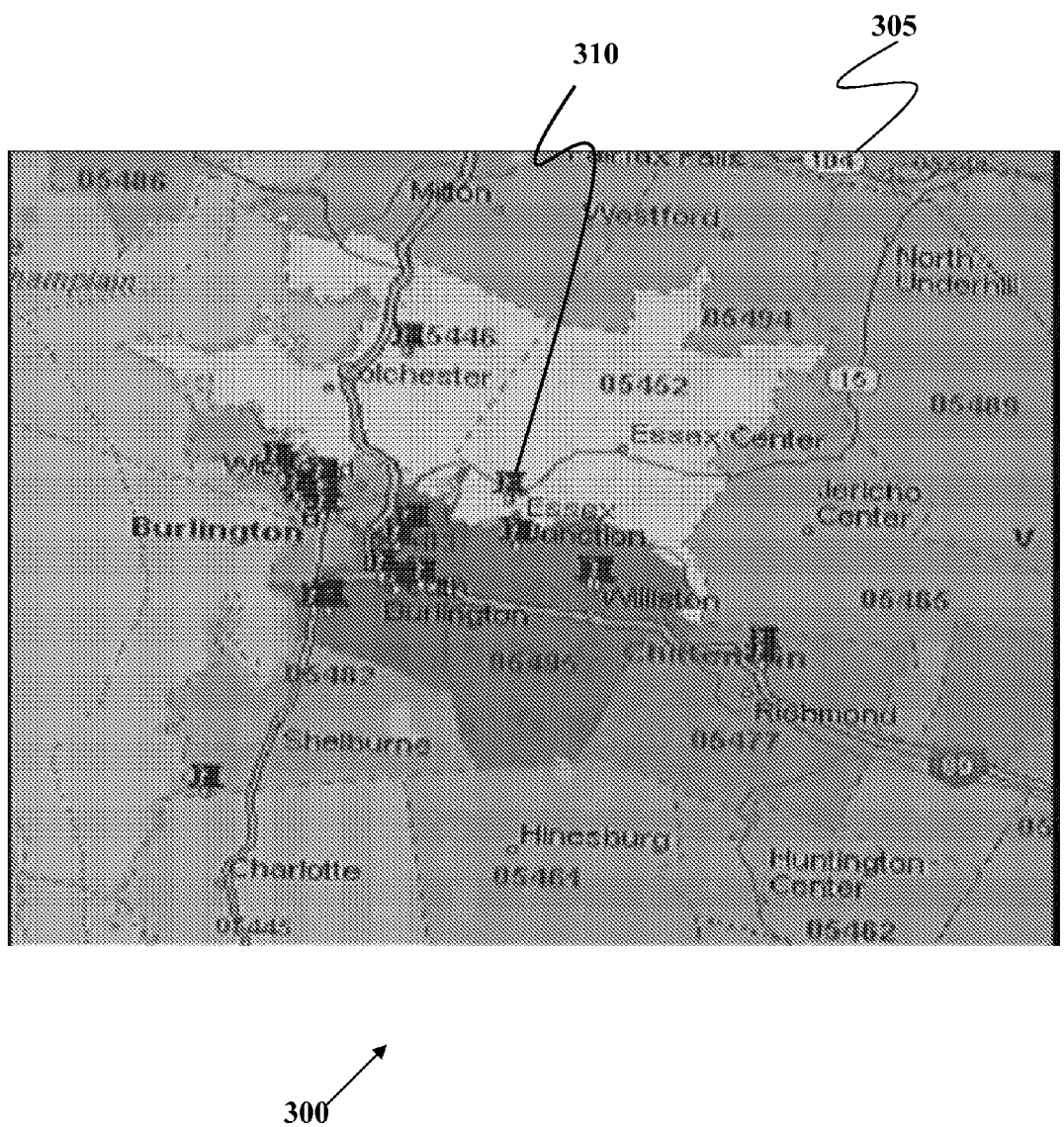
FIGS. 3-6 illustrate example healthcare services analysis and visualization systems.

FIG. 3 depicts an example healthcare analytics and visualization system 300. The system includes a user interface 305, such as a user-viewable representation of graphical geographic map. The user interface 305 displays a certain geographical region and provides one or more indicators 310 of healthcare services data within the region. In some examples, the scope of the region shown by the user interface 305 can be expanded and/or contracted (e.g., zoom in and/or zoom out). In some examples, a user can select an indicator 310 to retrieve further information regarding the location and/or data associated with the location.

Figure 4:
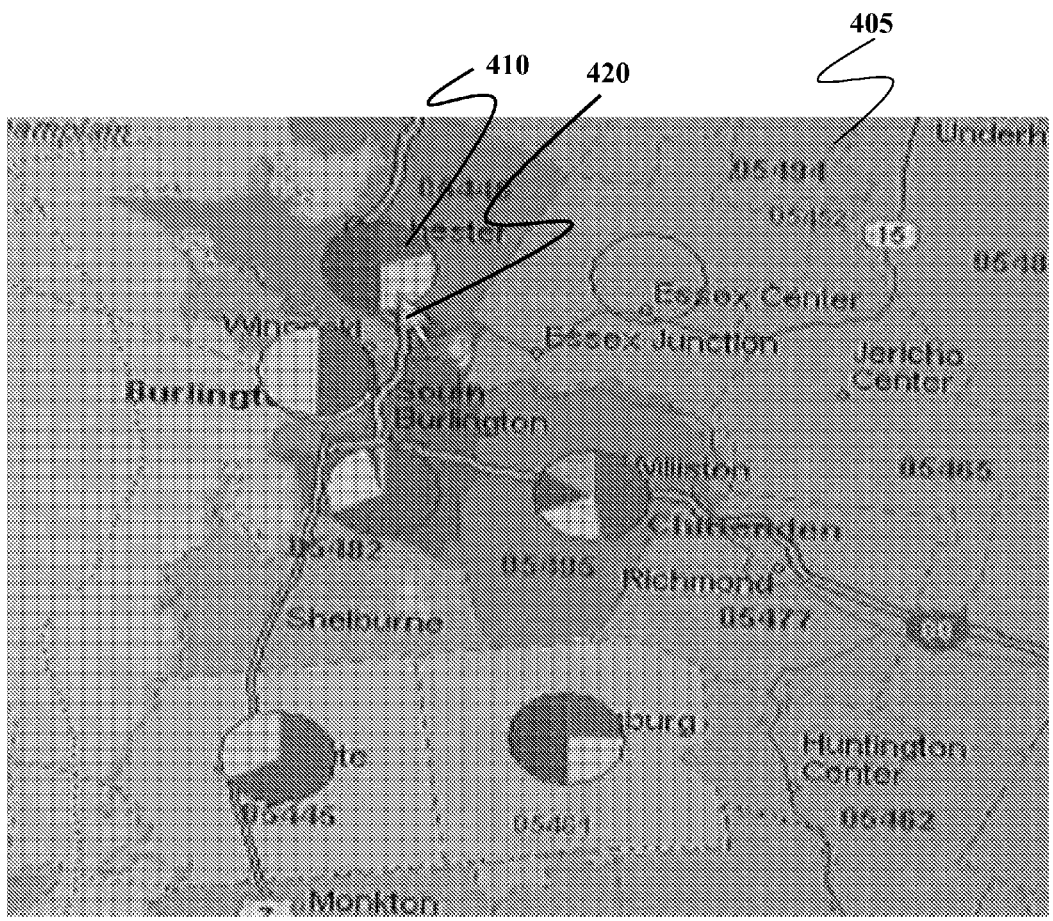

FIG. 4 depicts an example healthcare analytics and visualization system 400. The system includes a user interface 405, such as a user-viewable representation of graphical geographic map. The user interface 405 displays a certain geographical region and provides one or more indicators 410 (e.g., pie charts, graphs, etc.) representing healthcare services data within the region. In some examples, the scope of the region shown by the user interface 405 can be expanded and/or contracted (e.g., zoom in and/or zoom out). In some examples, a user can select an indicator 410, using the cursor 420 and/or other pointer, to retrieve further information regarding the location and/or data associated with the location. For example, a user can use the pointer 420 to select a pie chart indicator 410 to view additional information about the different segments of the pie chart 410 and the underlying data used to generate the indicator 410 via the user interface 405.

Figure 5:
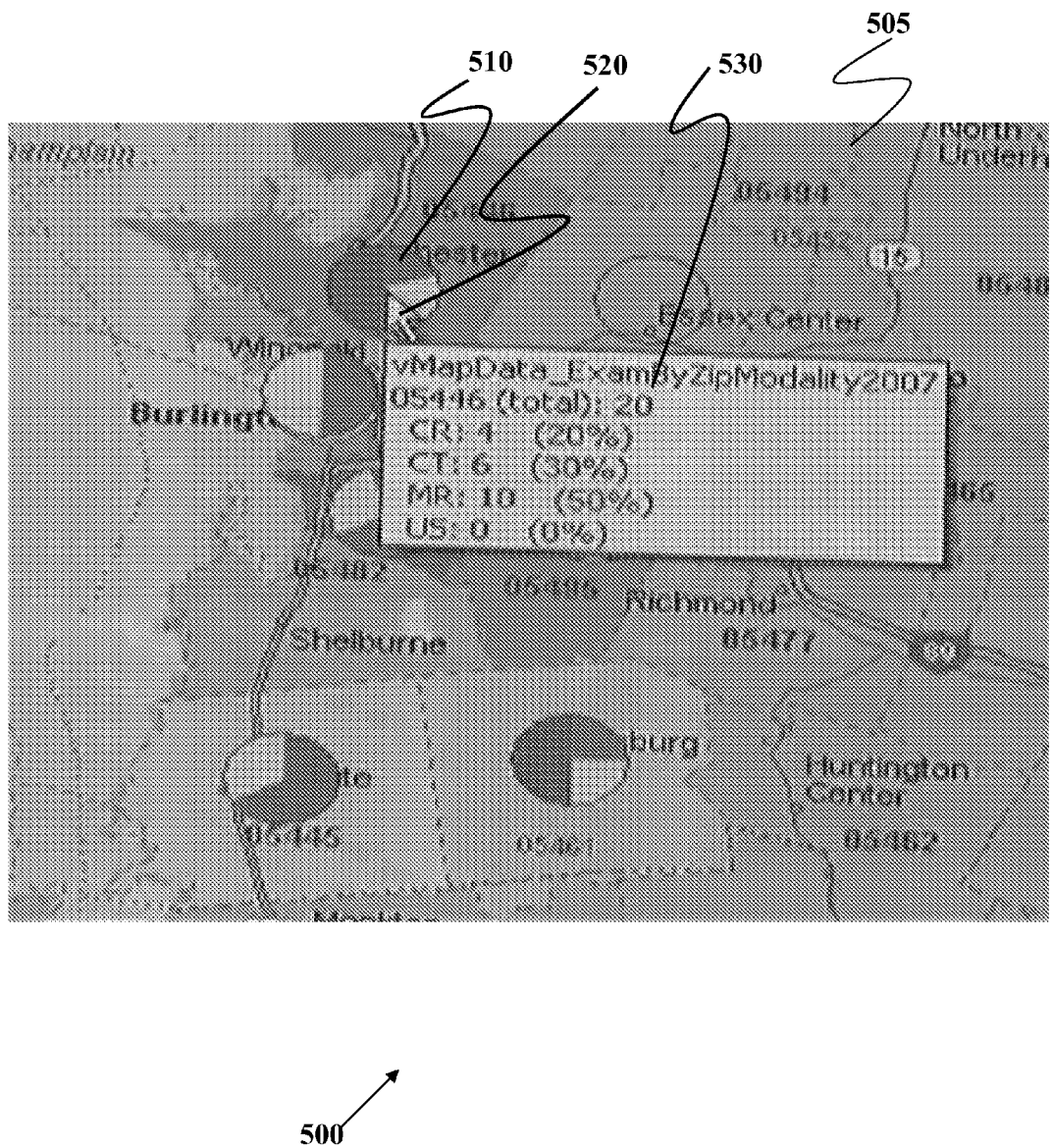

FIG. 5 shows another example of a healthcare analysis and visualization system 500. As shown in FIG. 5, by positioning a cursor 520 over and/or selecting an indicator 510 via a user interface 505, additional information 530 regarding the indicator 510 is displayed. For example, as shown in FIG. 5, a mouse-over of the cursor 520 with respect to the pie chart indicator 510 displays a box 530 showing the exam types (computed radiography (CR), computed tomography (CT), magnetic resonance (MR), and ultrasound (US) that make up the segments of the pie chart indicator 510 along with the raw data and their associated percentages for a given zip code. In some examples, by clicking on or otherwise selecting the indicator 510 and/or associated information 530, additional detail and/or underlying data can be displayed and/or accessed for review and modification.

Figure 6:
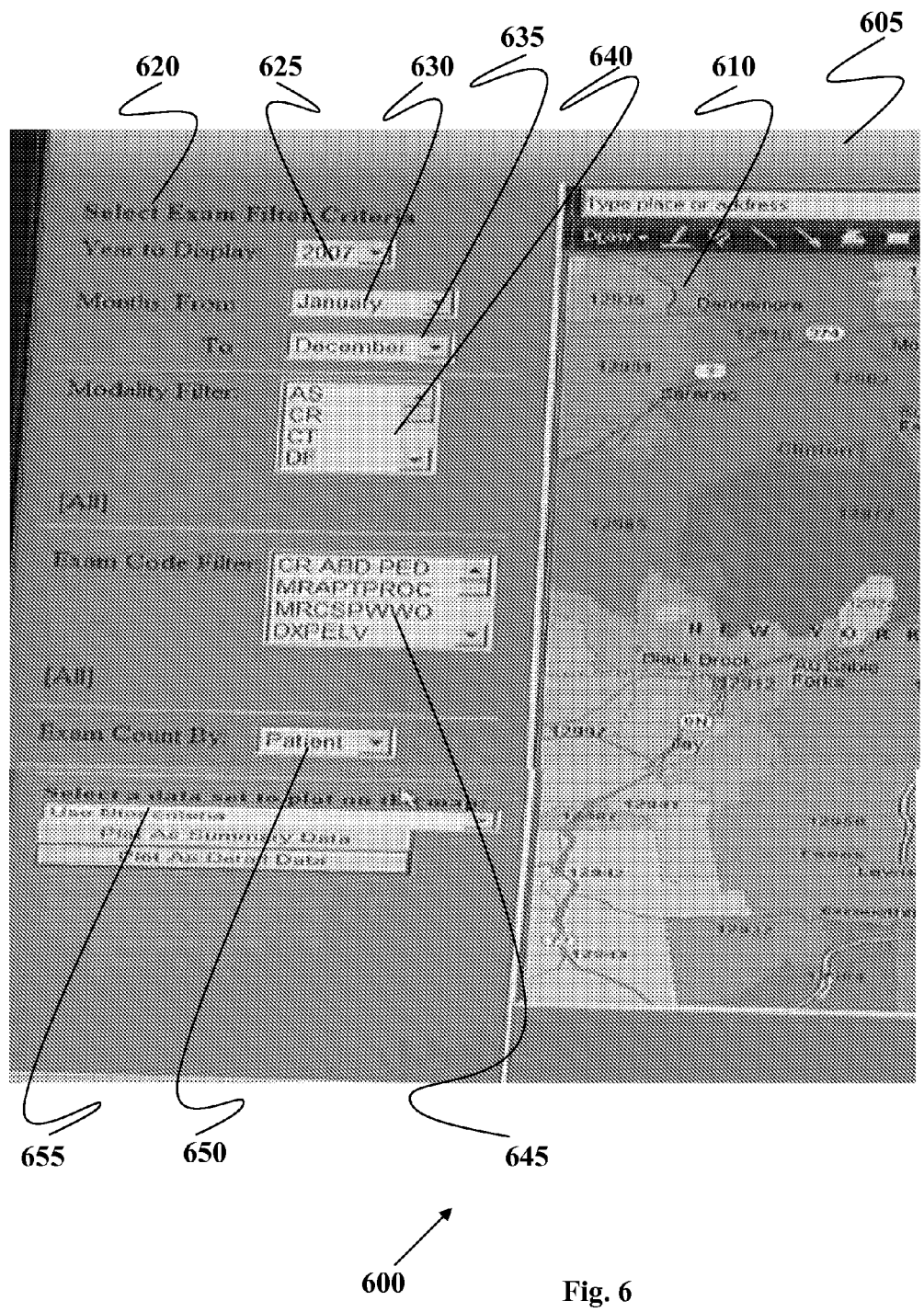

FIG. 6 illustrates an example healthcare services analysis and visualization system 600 including a user interface 605 having a geographical map representation or image 610 and a plurality of controls and/or configuration options 620-645. Controls and/or configuration options can include one or more exam selection criteria 620, for example. Exam selection criteria 620 can include one or more of a year 625, one or more months 630, 635 within the year 625 to display, a modality filter 640, an exam code filter 645, an exam count quantifier 650 (e.g., by patient, by facility, by region, etc.), and a data set selector 655, for example.

Figure 7:
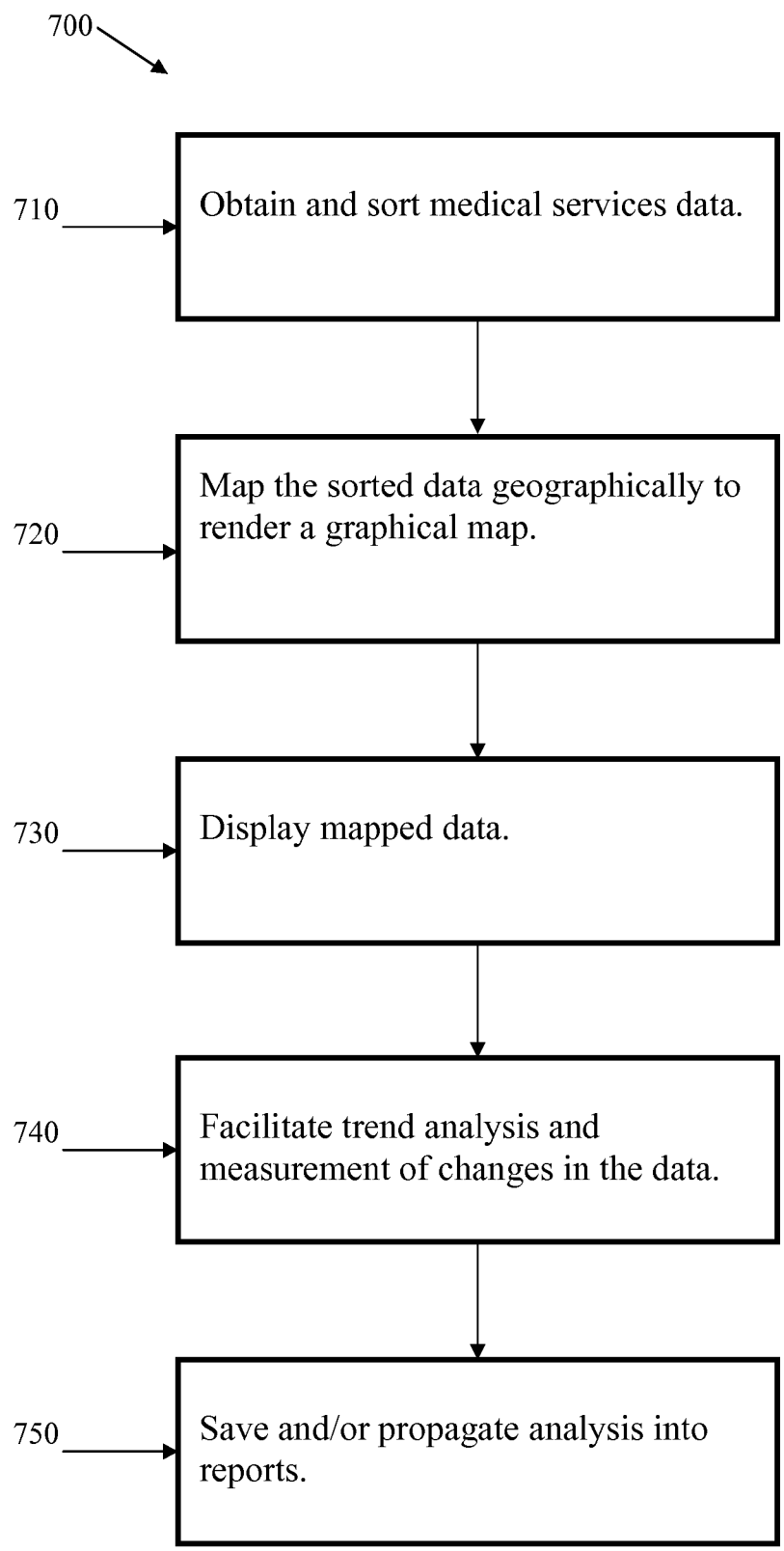
FIG. 7 illustrates a flow diagram for a method for virtual colonoscopy navigation using a mobile device.

FIG. 7 shows a flow diagram for a method 700 for visual mapping and analytics of healthcare services. At block 710, medical services data is obtained and sorted. For example, medical services data can be obtained from one or more RIS, EMR, PACS, and/or other data stores at one or more facilities in a region and/or healthcare enterprise and sorted based on one or more criteria such as date, region, enterprise, exam type, etc.

At block 720, the sorted data is geographically mapped to render a graphical map-based display of the information. For example, a map of a region can be overlaid with data and/or indicator(s) of data associated with that region. At block 730, the graphical map is displayed for user review.

At block 740, a user can interact with the geographical map display and the underlying data to conduct analysis of the data, trends within the data, etc. The user can interact with the map and its data to measure changes in the data based on one or more criteria (e.g., time, location, exam type, patient(s), etc.). A user interface displaying the mapped data and a processor or processing system providing the underlying data can support user review, analysis, reporting, etc., at one or more levels of granularity via the map, for example.

At block 750, resulting analysis, measurement, user comments/annotations, etc., can be saved and/or propagated into a report, for example. Data processing and/or user input can be used to drive supplemental processes and/or systems based on the mapped data, for example. Workflow simulation, resource allocation, staffing, servicing/repair, and/or other administrative process can be driven and/or assisted by the mapped data and associated analysis, for example.

As described herein, the method 700 can be implemented in one or more combinations of hardware, software, and/or firmware, for example. The method 700 can operate in conjunction with one or more external systems (e.g., data sources, healthcare information systems (RIS, PACS, CVIS, HIS, etc.), archives, imaging modalities, etc.). One or more components of the method 700 can be reordered, eliminated, and/or repeated based on a particular implementation, for example. The method 700 can be implemented using a stationary (e.g., desktop workstation, laptop computer, etc.) and/or mobile device (e.g., smartphone, tablet computer, etc.), for example.

Figure 8:
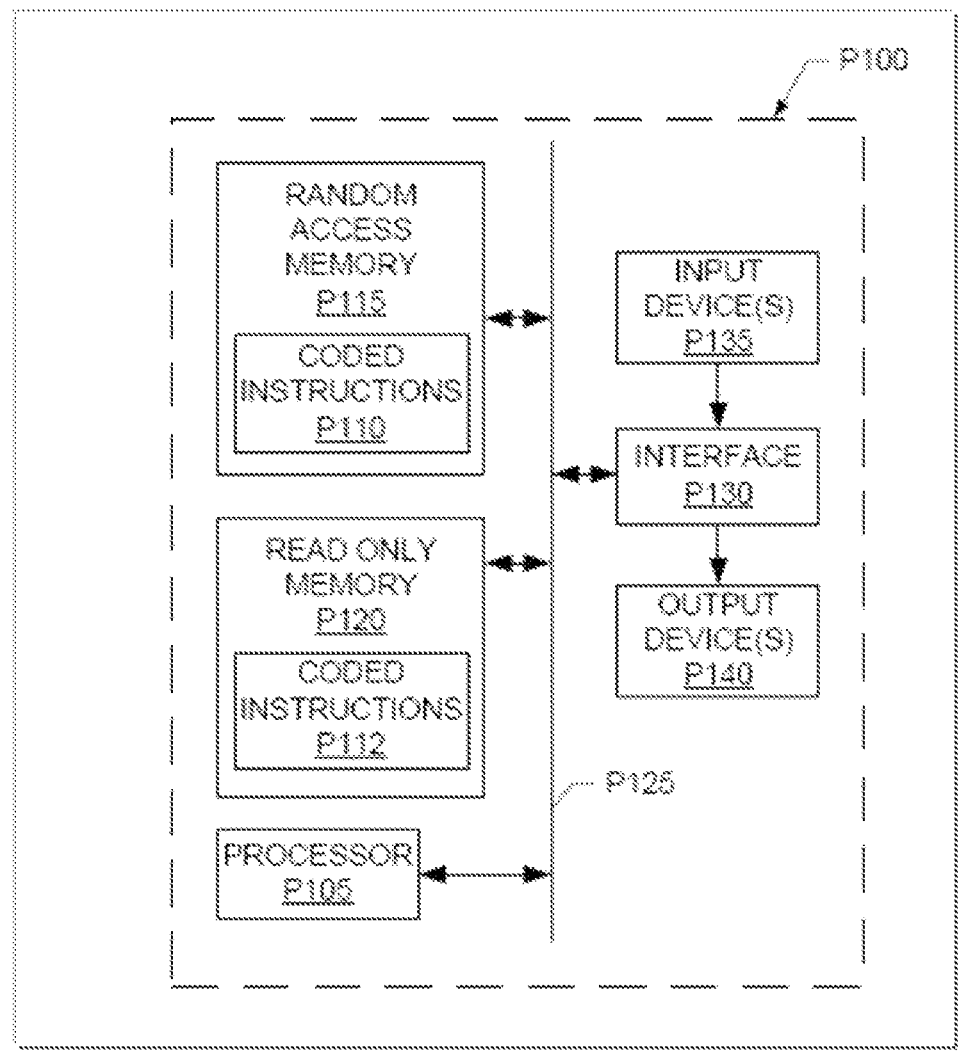
FIG. 8 is a schematic diagram of an example processor platform that can be used and/or programmed to implement example systems and methods described herein.

FIG. 8 is a schematic diagram of an example processor platform P100 that can be used and/or programmed to implement the example systems and methods described above. For example, the processor platform P100 can be implemented by one or more general-purpose processors, processor cores, microcontrollers, etc.

The processor platform P100 of the example of FIG. 8 includes at least one general-purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, the example process of FIG. 7 to implement the example methods and apparatus described herein.

The processor P105 is in communication with the main memory (including a ROM P120 and/or the RAM P115) via a bus P125. The RAM P115 may be implemented by dynamic random access memory (DRAM), synchronous dynamic random access memory (SDRAM), and/or any other type of RAM device, and ROM may be implemented by flash memory and/or any other desired type of memory device. Access to the memory P115 and the memory P120 may be controlled by a memory controller (not shown). The example memory P115 may be used to implement the example databases described herein.

The processor platform P100 also includes an interface circuit P130. The interface circuit P130 may be implemented by any type of interface standard, such as an external memory interface, serial port, general-purpose input/output, etc. One or more input devices P135 and one or more output devices P140 are connected to the interface circuit P130. The input devices P135 may be used to, for example, receive patient documents from a remote server and/or database. The example output devices P140 may be used to, for example, provide patient documents for review and/or storage at a remote server and/or database.

Thus, certain examples provide systems and methods to transform isolated data related to healthcare services into a visual, interactive, geographic map-based representation for user and/or system review. Certain examples facilitate trending and/or other measurement and/or analysis of the mapped data with or without user input via the geographic map-based representation. Certain examples help improve a healthcare services workflow and efficiency based on an analysis of the mapped healthcare services data by region, enterprise, etc. Certain examples help healthcare providers to analyze trends regarding from where their business is originating, such as from which primary care referring physician offices and where the patient goes for his or her initial medical exam. Certain examples help healthcare providers to analyze patient residence trends compared to the location(s) of their facilities to know how effective they are servicing the local market.

Patient and/or provider address/location information and clinical information can be retrieved, analyzed and displayed for user and/or automated system review and further action. A geographical map representation, such as Microsoft MapPoint™, can be used to display clinical information, filter it, identify specific information for one or more time periods of interest, and display it for a user, for example. Exams can be displayed based on one or more criteria such as zip code, patient, provider, etc. An exam count can be displayed based on zip code using a pie chart icon breaking down exams by modality, for example. Demographic information can be used to determine health care expenditure per zip code, for example. Such information can be overlaid on to a map to identify areas of high and low expenditure, for example. Existing business can be viewed and drilled down into for further information, trending, etc. Data and map views can be filtered by modality, exam code, household, patient, zip code, etc.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A healthcare services analysis and visualization system, the system comprising:
   a data store to store data related to healthcare services provided in at least one geographic region;
   a processor to retrieve and sort data from the data store based on one or more criteria, analyze the sorted data, and transform the sorted data into a geographical map representation of the healthcare services data; and
   a user interface to display the geographical map representation of the healthcare services data and facilitate user review and interaction with the geographical map representation and the underlying healthcare services data, wherein the healthcare services data is identified on the geographical map representation using one or more indicators, and wherein each of the one or more indicators is selectable by a user via the user interface to retrieve and view healthcare services data and analysis associated with the indicator, wherein the processor is to generate geographic trend information for display and user access via the geographical map representation based on the sorted healthcare services data, the geographic trend information provided in conjunction with radiology business data to create a visual business and planning tool.

2. The system of claim 1, wherein the processor is to generate a report based on the geographical map representation and the underlying healthcare services data.

3. The system of claim 1, wherein the one or more indicators comprise one or more pie chart indicators.

4. The system of claim 1, wherein the healthcare services data is sorted based on one or more criteria including at least one of zip code, healthcare services provider, and exam type.

5. The system of claim 1, wherein the geographical map representation is focused on a region and wherein the user interface allows the user to zoom in and out of the region.

6. The system of claim 1, wherein the data store comprises a radiology information system.

7. The system of claim 1, wherein the trend information comprises an analysis of trends regarding patient residence and healthcare facility location.

8. The system of claim 7, wherein the trend information comprises an analysis of trends regarding patient income and patient proximity to healthcare facility location to visualize an impact of the healthcare facility on at least one geographic region.

9. A method for analysis, mapping, and visualization of healthcare services data, the method comprising:

retrieving healthcare services data from a data store;

sorting the retrieved healthcare services data, using a processor, based one or more criteria;

analyzing the sorted data, using a processor, according to one or more criteria;

transforming the sorted data into a geographical map representation of the healthcare services data using a processor;

displaying the geographical map representation of the healthcare services data via a user interface; and facilitating user review and interaction with the geographical map representation and the underlying healthcare services data via the user interface, wherein the healthcare services data is identified on the geographical map representation using one or more indicators, and wherein each of the one or more indicators is selectable by a user via the user interface to retrieve and view healthcare services data and analysis associated with the indicator, wherein the processor is to generate geographic trend information for display and user access via the geographical map representation based on the sorted healthcare services data, the geographic trend information provided in conjunction with radiology business data to create a visual business and planning tool.

10. The method of claim 9, further comprising generating a report based on the geographical map representation and the underlying healthcare services data.

11. The method of claim 9, wherein the one or more indicators comprise one or more pie chart indicators.

12. The method of claim 9, wherein the healthcare services data is sorted and analyzed based on one or more criteria including at least one of zip code, healthcare services provider, and exam type.

13. The method of claim 9, wherein the geographical map representation is focused on a region and wherein the user interface allows the user to zoom in and out of the region.

14. The method of claim 9, wherein the trend information comprises an analysis of trends regarding patient residence and healthcare facility location.

15. The method of claim 14, wherein the trend information comprises an analysis of trends regarding patient income and patient proximity to healthcare facility location to visualize an impact of the healthcare facility on at least one geographic region.

16. A non-transitory computer-readable storage medium having a set of instructions stored thereon which, when executed, instruct a processor to implement a healthcare services analysis and visualization system, the system comprising:

a data store to store data related to healthcare services provided in at least one geographic region;

a processor to retrieve and sort data from the data store based on one or more criteria, analyze the sorted data, and transform the sorted data into a geographical map representation of the healthcare services data; and a user interface to display the geographical map representation of the healthcare services data and facilitate user review and interaction with the geographical map representation and the underlying healthcare services data, wherein the healthcare services data is identified on the geographical map representation using one or more indicators, wherein each of the one or more indicators is selectable by a user via the user interface to retrieve and view healthcare services data and analysis associated with the indicator, and wherein the processor is to generate geographic trend information for display and user access via the geographical map representation based on the sorted healthcare services data, the geographic trend information provided in conjunction with radiology business data to create a visual business and planning tool.

17. The computer-readable storage medium of claim 16, wherein the healthcare services data is identified on the geographical map representation using one or more indicators selectable by a user via the user interface to retrieve and view healthcare services data and analysis associated with the indicator.

18. The computer-readable storage medium of claim 16, wherein the healthcare services data is sorted based on one or more criteria including at least one of zip code, healthcare services provider, and exam type.

* * * * *